United States Patent [19]
Buckley

[11] 4,372,691
[45] Feb. 8, 1983

[54] METHOD AND APPARATUS FOR DETERMINING THE THERMAL RESISTANCE OF A STRUCTURE SUCH AS A WALL CEILING OR THE LIKE

[75] Inventor: Robert E. Buckley, Norwalk, Conn.

[73] Assignee: Barnes Engineering Company, Stamford, Conn.

[21] Appl. No.: 231,664

[22] Filed: Feb. 5, 1981

[51] Int. Cl.³ .......................................... G01N 25/18
[52] U.S. Cl. ................................................... 374/44
[58] Field of Search ................. 73/15 A, 15 R, 190 H

[56] References Cited
U.S. PATENT DOCUMENTS

| | | | |
|---|---|---|---|
| 2,878,669 | 3/1959 | Knudson et al. | 73/15 |
| 4,236,403 | 12/1980 | Poppendiek | 73/15 |

Primary Examiner—Herbert Goldstein
Attorney, Agent, or Firm—Parmelee, Bollinger & Bramblett

[57] ABSTRACT

The inside air temperature, the outside air temperature and the temperature of the inside surface of an exterior structure whose 'R' value is to be determined and these values are selectively applied to the 'R' value apparatus which stores the inside and outside temperatures as voltage analogs and combines them to provide a first difference signal. The inside temperature analog is also applied to a second combination circuit. After the inside and outside temperature analogs are fed to the apparatus and stored therein, then the inside surface temperature of the structure, such as the wall or ceiling, which is being measured, is applied as an analog voltage to the apparatus. The inside structure temperature analog is combined with the inside room temperature analog to provide a second difference signal which is then divided into the first difference signal in an analog divider, a portion of the output being fed directly to a meter calibrated in 'R' values.

7 Claims, 2 Drawing Figures

METHOD AND APPARATUS FOR DETERMINING THE THERMAL RESISTANCE OF A STRUCTURE SUCH AS A WALL CEILING OR THE LIKE

BACKGROUND OF THE INVENTION

This invention relates to a method and apparatus for providing a noncontact, direct reading method of measuring the 'R' value or thermal resistance of a structure such as a wall, ceiling, or the like.

Since heat loss is normally measured in BTU's per square foot per hour, it is convenient to use a signal representative number for an 'R' value which is representative of the thermal resistance to heat flow to enable energy auditors, insulation contractors, building inspectors, maintenance personnel and the like to measure heat loss in order to provide preventive maintenance and energy management programs. Accordingly, the 'R' value or thermal resistance is the standard index for the insulation efficiency of a building or of an insulating material. The measurement of the 'R' value normally requires readings of inside and outside temperatures from which the 'R' value is computed. No method has been provided for directly reading this value. Prior methods require several temperature measurements and the use of associated graphs in order to provide an estimate of a usable 'R' value.

SUMMARY OF THE INVENTION

Accordingly, it is an object of the present invention to provide a direct reading, noncontact method of measuring the 'R' value or thermal resistance of a structure.

A further object of this invention is to provide a direct reading, noncontact measurement of the thermal resistance of a structure such as a wall, ceiling or the like.

Still a further object of this invention is to provide a new and improved method and apparatus for measuring the 'R' value of a wall which is simple, reliable and less time consuming than previous methods and apparatus utilized for this purpose.

Still another object of this invention is to provide a new and improved method and apparatus for measuring the thermal resistance of materials which provides immediate and on site readings.

In carrying out this invention in one illustrative embodiment thereof, a method is provided which involves measuring the 'R' value of a material by measuring the inside room temperature and storing that temperature analog in an instrument having a direct reading meter. The outside background temperature is then measured and stored as an analog voltage in the instrument, and the inside room and the outside background temperature analogs are combined to provide a first difference signal. The inside temperature of the structure whose 'R' value is to be determined is then measured and applied to the instrument where the inside structure temperature analog is combined with the inside room temperature analog to provide a second difference signal. The first difference signal is divided by the second difference signal in an analog divider and a portion of the divided signal is applied directly to the meter for providing a direct reading 'R' value representing the thermal resistance of the material being measured. In a preferred form storage is provided on potentiometers by adjusting the potentiometer to provide a null reading on the 'R' meter. The 'R' meter to which the signals are applied, stored and computed may be used in conjunction with an infrared radiometer which provides the readings therefor.

BRIEF DESCRIPTION OF THE DRAWINGS

The invention, together with further objects, aspects, features and advantages thereof will be best understood from the following description taken in conjunction with the accompanying drawings.

DESCRIPTION OF THE PREFERRED EMBODIMENTS

The 'R' value or thermal resistance is a commonly employed standard index for the insulation efficiency of a building or of an insulating material. For example the 'R' value or resistance to heat flow of three inches of fiberglass has an 'R' value of 11 while a typical residential wall measured at a stud should have an 'R' value of 7 to 8. The 'R' value may be determined by solving the equation $$R = R_a \left[ \frac{t_i - t_o}{t_i - t_s} \right]$$

where $R_a$ is the Resistivity of the air film on the inner surface of the insulator or interior wall being measured, $t_i$ is the inside air temperature, $t_o$ is the outside air temperature and $t_s$ is the temperature of the inside surface of an exterior wall. The 'R' value has units which are expressed in $$\frac{°F. - Hr - ft^2}{BTU}$$

which are awkward and accordingly the 'R' value is expressed simply in terms of a whole number. Heat transfer in BTU's per hour can be calculated from the area considered, the temperature difference and the 'R' value. Accordingly, the 'R' value is typical both in the measurement of heat transfer as well as providing an indication of resistance to heat flow of walls, ceilings, etc. which provide an indication of the insulation quality and/or heat loss of a particular wall or structure.

Utilizing the above equation, it will be apparent that in order to provide an 'R' value three temperature measurements are required:

(1) The inside temperature obtained by measuring the temperature of an object in the room, for example a chair, a lamp, a piece of paper, etc.
(2) The measured outside background temperature and
(3) The measured temperature of the inside surface of the external wall whose 'R' value is desired to be determined.

Figure 1:
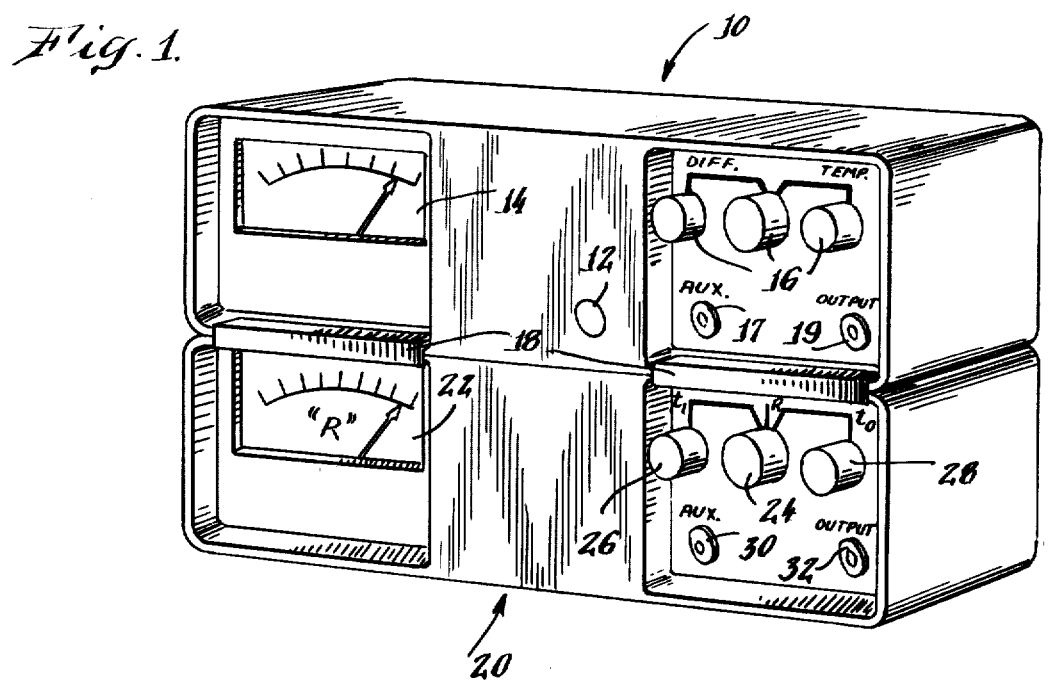
FIG. 1 is a perspective view of the 'R' meter of the present invention mounted on and utilized with an infrared thermometer.

Referring now to FIG. 1, a noncontact temperature measuring instrument, referred to generally with the reference character 10, is conveniently attached by friction clips 18 to an 'R' meter, referred to generally with the reference character 20. The temperature measuring instrument 10 may be of any suitable type and its function is to provide an analog output which corresponds to temperature. One type of temperature measuring instrument which is particularly suitable for the present application is an infrared radiometer Model No. 14-220 sold under the tradename Instatherm which is manufactured by Barnes Engineering Company, Stamford, Connecticut, the assignee of the present invention. The present invention however may utilize any type of contact or noncontact temperature measuring device which provides an analog output representing temperature which may be fed to the 'R' meter 20.

The radiometer 10 shown in FIG. 1 includes a viewfinder 12 for aiming the instrument, a meter 14 which may be provided with multiple scales, a plurality of knobs 16 for providing the appropriate setting, switching and the desired operating functions and includes an auxiliary input terminal 17 and an output terminal 19. As has been pointed out this instrument is conventional and accordingly will not be described in detail. The important function of the radiometer 10 is to provide an analog voltage from the output terminal 19 which may be fed to the 'R' meter 20 in accordance with the temperatures which are desired to be measured and utilized in the 'R' meter.

The 'R' meter 20 includes a meter 22, control knobs 24, 26, 28 and input and output terminals 30 and 32, respectively. Control knob 24 operates a three position, two pole switch 34, control knob 26 sets and stores temperature $t_i$ while knob 28 sets and stores temperature $t_o$ in the 'R' meter. Switch 34 is illustrated as a two pole switch for illustrative purposes to simplify the description. In practice a six pole switch is employed to provide battery check functions and the like (not shown).

Figure 2:
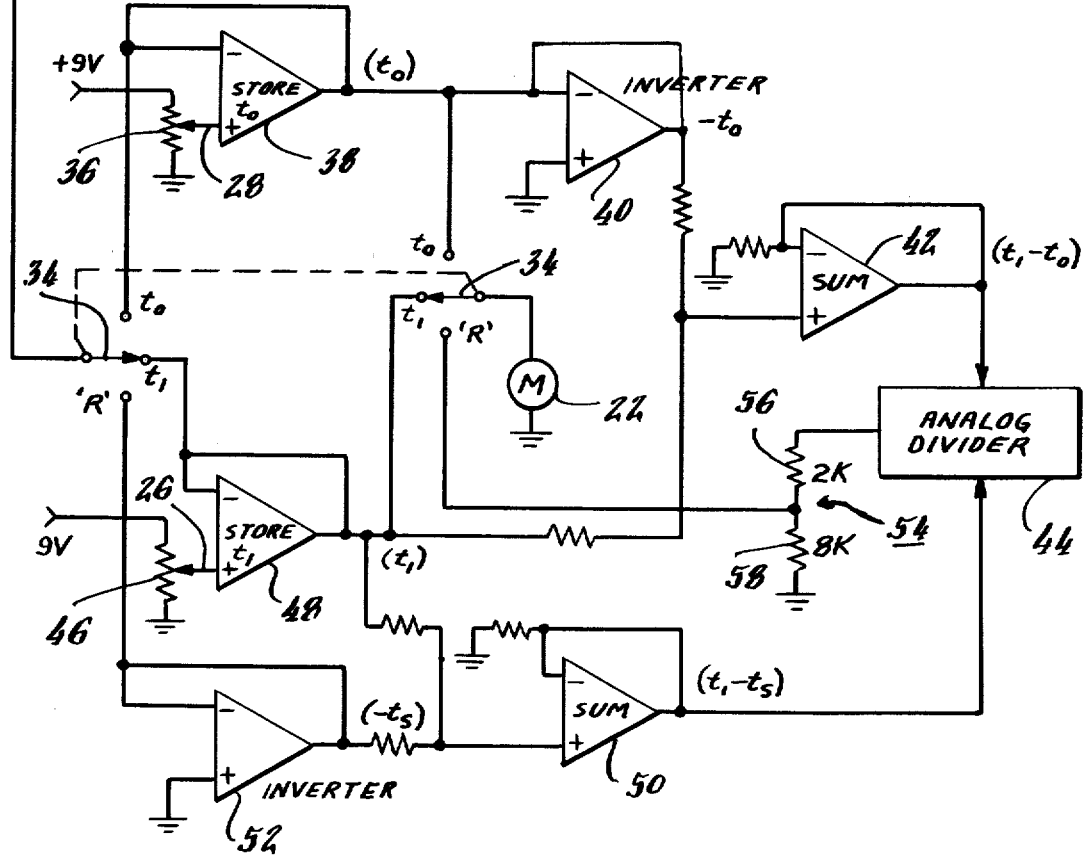
FIG. 2 is an electrical schematic diagram of the 'R' meter embodying the present invention.

Referring now to FIG. 2, the 'R' meter 20, in addition to the three position, two pole switch 34 to which the temperature analog voltage is applied from the radiometer 10 includes the first potentiometer 36 which is adjusted by the knob 28. The set output of the potentiometer 36 is applied to an operational amplifier 38 where it is stored. The output of amplifier 38 corresponding to the temperature analog signal voltage of temperature $t_o$ is applied to an inverter 40 which is coupled to a summer 42 whose output is applied to an analog divider 44. A second potentiometer 46 which is adjusted by knob 26 is applied to operational amplifier 48. The output of the operational amplifier 48 is applied to a summer 50 whose output is coupled to the analog divider 44. In the 'R' position of the switch 34 the temperature analog signal voltage which in the 'R' position will be analog temperature $t_s$ is applied to an inverter 52 whose output is also applied to the summer 50. The output of the analog divider 44 is applied to a voltage divider 54 having resistors 56 and 58 therein, the divided output being applied to the 'R' meter 22.

By utilizing the temperature measuring instrument of the radiometer 10, which provides an analog voltage output corresponding to temperature, to make the temperature measurements of $t_i$, $t_s$ and $t_o$ and setting a given proportion on voltage divider 54 for approximating $R_a$, in the aforesaid formula for example 0.8, the 'R' value may be read directly on meter 22.

In operation the radiometer output from terminal 19 is coupled to the 'R' meter 20 input 30 by a suitable jumper which is not shown in FIG. 1 for ease of illustration. The control knob 24 on the 'R' meter 20 which controls switch 34 is set to the $t_o$ position and the radiometer 10 is aimed at an object that is at outside air temperature through the viewfinder 12. The outside air temperature analog $t_o$ is applied through the amplifier 38 as well as to the meter 22 which has been switched to the output of the amplifier 38 by the three position, two pole switch 34. The temperature analog $t_o$ is then stored as a voltage determined by the resistance of the potentiometer 36 by nulling the output of the amplifier 38 as indicated on the meter 22.

The switch 34 is then switched to the $t_i$ position and the radiometer 10 is directed at an object inside the room to provide an inside room temperature $t_i$ which is applied to the amplifier 48. Temperature $t_i$ is stored as the voltage analog in potentiometer 46 by nulling the output of amplifier 48 on the meter 22. Switch 34 is then set to the 'R' position, and the radiometer 10 is aimed at the inside wall surface of an exterior wall whose 'R' value is desired to be determined.

With the switch 34 in the 'R' position, the wall surface temperature analog $t_s$ is inverted by the inverter 52 and summed with the stored temperature analog $t_i$ in the summer 50 to produce an output therefrom of $t_i$-$t_s$. At the same time, simultaneously therewith the stored analog signal $t_o$ is inverted by the inverter 40 and summed with analog signal $t_i$ in the summer 42 to produce an output therefrom of $t_i$-$t_o$. The signals from the output of the summer 42 and the summer 50 namely $t_i$-$t_o$ and $t_i$-$t_s$, respectively, are brought to two ports of an analog divider 44 where $t_i$-$t_o$ is divided by $t_i$-$t_s$. The output or the quotient of the analog divider 44 is applied to the voltage divider 54 where a portion of the quotient determined by resistance 58 divided by resistance 56 plus resistance 58, e.g. 0.8 times, is applied to the meter 22. The resulting signal which represents $$.8\left[\frac{t_i - t_o}{t_i - t_s}\right]$$

is displayed on meter 22 which is calibrated in 'R' value from 0.5 to 50. Analog divider 44 has an exponential capacity which may be used to raise its output to a fractional power e.g. 0.4 which linearizes the scale of 'R' values for easier reading on the analog meter 22. Although an analog meter 22 is shown, a digital meter can be provided if desired.

In summary the simple operating procedure is as follows.

(1) Observe the outside air temperature and store that analog value in the 'R' meter 20 by nulling the $t_o$ potentiometer;

(2) Observe the inside air temperature and store that value in the 'R' meter by nulling the $t_i$ potentiometer; and (3) Observe the inside wall temperature of the exterior wall and feed the signal to the 'R' meter which calculates and displays the 'R' value.

It should also be pointed out that a hot/cold switch may be included for revising the polarities of $t_o$ and $t_i$ in order to permit 'R' value measurements in air conditioning situations as well as heating situations.

Accordingly, by simply providing three temperature measurements, the 'R' value can be estimated and read directly from a meter without requiring any interpretation or interpolation using graphs and tables. Using a radiometer of the noncontact type, permits temperature measurements where physical contact is either impossible, hazardous or undesirable. Through the use of a direct value reading and noncontact temperature measurement, energy auditing procedures are simplified and provide on site measurements.

Since other changes and modifications varied to fit particular operating requirements and environments will be apparent to those skilled in the art, the invention is not considered limited to the examples chosen for purposes of illustration, and covers all changes and modifications which do not constitute a departure from the true spirit and scope of this invention.

What is claimed is:

1. An 'R' value meter for providing a direct reading, noncontact measurement of the thermal resistance of a structure such as a wall, ceiling or the like after the inside room temperature and the outside temperature are applied thereto comprising:
   first storage means for storing the inside room temperature signal applied thereto,
   second storage means for storing the outside temperature signal applied,
   first means for combining the outputs of said first and second storage means to provide a first difference signal,
   second means for combining a signal representing the inside surface temperature of the structure whose 'R' value is desired to be determined, and the output of said first storage means to provide a second difference signal,
   divider means for dividing said first difference signal by said second difference signal,
   a meter, and
   means for coupling a portion of the output of said divider means to said meter for providing a direct 'R' value reading which is indicative of the thermal resistance of the structure being measured.

2. The 'R' value meter set forth in claim 1 wherein said first and second storage means are potentiometers.

3. The 'R' value meter set forth in claims 1 or 2 having a three position switch means for applying said inside room temperature signal to said first storage means in a first position; for applying said outside temperature signal to said second storage means in a second position; and for applying the structure temperature signal to said second means and coupling said meter to divider means in a third position.

4. The 'R' value meter set forth in claim 1 or 2 having a radiometer coupled thereto applying analog temperature signals for said outside air temperature, inside room temperature and said structure surface temperature to the input for said 'R' meter.

5. A direct reading, noncontact method of measuring the 'R' value or thermal resistance of a structure comprising the steps of:
   measuring the inside room temperature of an object within the room,
   storing the inside room temperature signal in an instrument having a direct reading meter,
   measuring the outside background temperature,
   storing the outside background temperature signal in said instrument,
   subtracting the outside background temperature signal from the inside room temperature signal to provide a first difference signal,
   measuring the surface temperature on the inside of the structure whose 'R' value is to be determined,
   applying said temperature measurement signal to said instrument,
   subtracting said structure temperature signal from said inside room temperature signal to provide a second difference signal,
   dividing said first difference signal by said second difference signal and
   applying a fixed proportion of the divided signal directly to said meter for providing a direct reading 'R' value representing the thermal resistance of the structure being measured.

6. The method set forth in claim 5 wherein the steps of storing the inside room temperature and the outside background temperatures comprises setting potentiometers in said instrument.

7. The method set forth in claim 6 wherein the steps of setting the potentiometers comprises nulling the temperature reading in said instrument.

* * * * *